United States Patent [19]

Jevne et al.

[11] Patent Number: 5,176,956

[45] Date of Patent: Jan. 5, 1993

[54] BIOMEDICAL APPARATUS HAVING FATTY ACID DIMER DERIVED SKIN-COMPATIBLE ADHESIVE COMPOSITION THEREON

[75] Inventors: Allan H. Jevne, Anoka; Arthur J. Coury, St. Paul; Patrick T. Cahalan, Champlin, all of Minn.

[73] Assignee: Medtronic, Inc., Minneapolis, Minn.

[21] Appl. No.: 737,791

[22] Filed: Jul. 1, 1991

Related U.S. Application Data

[63] Continuation of Ser. No. 256,086, Oct. 4, 1988, abandoned, which is a continuation of Ser. No. 143,259, Jan. 4, 1988, abandoned, which is a continuation of Ser. No. 655,273, Sep. 26, 1984, abandoned.

[51] Int. Cl.⁵ .............................................. B05D 3/12
[52] U.S. Cl. ..................................... 128/640; 428/375; 428/355; 604/344; 604/20; 604/307; 528/44; 528/74.5; 128/802; 602/54; 424/448
[58] Field of Search ................ 428/375, 355; 128/155, 128/156, 639, 640, 641, 798; 604/344; 528/44, 74.5

[56] References Cited

U.S. PATENT DOCUMENTS

| | | | |
|---|---|---|---|
| Re. 24,906 | 12/1960 | Ulrich | 526/328.5 |
| 3,085,577 | 4/1963 | Berman et al. | 128/641 |
| 3,493,534 | 2/1970 | Coury et al. | 528/196 |
| 3,549,570 | 12/1970 | Coury | 528/195 |
| 3,799,965 | 3/1974 | Mackay et al. | |
| 4,027,664 | 6/1977 | Heavner, Jr. | 128/417 X |
| 4,108,814 | 8/1978 | Reiff et al. | 524/840 |
| 4,125,110 | 11/1978 | Hymes | 524/55 |
| 4,156,067 | 5/1979 | Gould | 128/156 |
| 4,166,051 | 8/1979 | Cilento et al. | 604/336 |
| 4,192,785 | 3/1980 | Chen et al. | 604/344 |
| 4,258,715 | 3/1981 | Goble | 524/387 |
| 4,284,506 | 8/1981 | Tetenbaum et al. | 528/74.5 |
| 4,306,551 | 12/1981 | Hymes | 524/55 |
| 4,423,179 | 12/1983 | Guagliardo | 525/440 |
| 4,455,146 | 6/1984 | Noda et al. | 428/335 |
| 4,460,371 | 7/1984 | Abber | 428/335 |
| 4,564,010 | 1/1986 | Coughlan et al. | 428/335 |
| 4,580,339 | 4/1986 | Ioffe | 128/641 |
| 4,775,374 | 10/1988 | Cilento et al. | 604/344 |

FOREIGN PATENT DOCUMENTS 3239318 10/1982 Fed. Rep. of Germany .
1023390 3/1966 United Kingdom .

*Primary Examiner*—Patrick J. Ryan
*Assistant Examiner*—N. Edwards
*Attorney, Agent, or Firm*—Harold R. Patton; Daniel W. Latham

[57] ABSTRACT

An improved biomedical appliance having disposed on a skin-contacting, operant portion thereof, a film or layer of a skin compatible, tacky, pressure sensitive polymeric adhesive, the reaction product consisting of at least one fatty acid dimer based or derived component and a suitable co-reactant. Electrodes, surgical tapes, TENS devices and iontophoresis devices employing the adhesive are disclosed.

32 Claims, No Drawings

BIOMEDICAL APPARATUS HAVING FATTY ACID DIMERDERIVED SKIN COMPATIBLE ADHESIVE COMPOSITION THEREON

This is a continuation of copending application Ser. No. 07/256,086 filed on Oct. 4, 1988 is now abandoned which is a continuation of Ser. No. 07/143,259, filed Jan. 4, 1988 now abandoned which is a continuation of Ser. No. 07/655,273 filed on Sep. 26, 1984, now abandoned.

This invention relates to improved biomedical appliances. More particularly, this invention relates to new and improved biomedical apparatus having on an operative surface or operative portion thereof a particularly advantageous skin compatible, tacky or pressure sensitive, self-supporting, water resistant biomedical adhesive. Even more particularly, this invention relates to an improved biomedical appliance having on an operative surface thereof a hydrophobic, biomedical adhesive comprising the reaction product of a fatty acid or fatty acid-derived, substantially difunctional dimer and particular co-reactants or co-monomers. In a preferred practice of the invention, a third co-reactant, viz, a cross-linking agent is also included.

BACKGROUND OF THE INVENTION

There are many patents in the field of biomedical appliances. This area has been the subject of intense research in the last several years, resulting in the issuance of many United States and other patents. A representative but by not means a complete list of such patents include U.S. Pat. Nos. 4,306,551 issues to Hymes et al entitled "Sterile Improved Bandage and Sealant"; 4,258,715 issued to Goble entitled "Radiation Crosslinked Acrylamide Polymer Compositions and Shaped Articles Therefrom"; 4,231,369 issued to Sorensen et al entitled "Sealing Material for Ostomy Devices"; 4,125,110 issued to Hymes entitled "Monitoring and Stimulation Electrode"; 4,253,460 issued to Chen et al entitled "Ostomy Adhesive"; Re24,906 to Ulrich entitled "Pressure Sensitive Adhesive Sheet Material", among others. The terms "biomedical apparatus or appliance" or "biomedical device" as used herein are intended to be very broad. These terms are specifically intended to include, without limitation, essentially any device which is intended to be affixed, or adhered in any manner to a patient's skin. Thus these terms include, without limitation, ostomy appliances, electrodes, bandages, iontophoresis devices and transcutaneous electronic nerve stimulation (TENS) devices. The adhesive herein described would generally be disposed about the perimeter of a particular device, e.g., a TENS device, so as to hold it in contact with the skin.

BRIEF SUMMARY OF THE INVENTION

Briefly, in one aspect, the present invention is a biomedical apparatus, device or appliance having disposed on at least a portion of an operant surface thereof a layer, film or body of a polymeric, substantially hydrophobic, pressure sensitive or inherently tacky, skin-compatible, adhesive composition consisting essentially of a reaction product of:
1. a substantially difunctional, fatty acid or fat acid-derived dimer, preferably having a molecular weight in the range of about 300 to about 1,000 more preferably 400 to 800; and
2. a compatible, polymer-forming co-reactant or co-monomer selected from the group consisting of a second fatty acid derived dimer as described in 1; diols, polyols, diamines, polyamines, polyether-polyols, polyester-polyols, isocyanates, esters, acids, acid chlorides, chloroformates, carbonates or mixtures thereof.

In a preferred practice, the total fatty acid dimer or derivative based content of the reaction product/biomedical adhesive composition is generally about 50 to about 99 weight percent. In a another aspect of the instant invention, the biomedical composition of the biomedical appliance includes from 0 to about 10 equivalent percent (preferably from about 2 to 4 equivalent percent) of a third co-reactant or crosslinking agent. In yet another practice of the present invention, tackifiers, humectants, extenders, binders or other additives which enhance the properties of skin-compatibility, tack, hydrophobicity/hydrophilicity, coherence or some other aspect or property of the adhesive may be added. As the term is used herein, "operant surface" of the biomedical apparatus or appliance is intended to mean that portion of the appliance or device (it may include the entire device) which engages and complies or cooperates with the skin of a patient to provide support for the apparatus disposed thereon. "Skin compatible" as the term is used herein means capable of remaining in contact with skin so as to provide support or adhesion for a biomedical appliance or device for a suitable time period without generating significant skin irritation. Skin-compatible also means that the instant biomedical adhesive has sufficient cohesive strength so that when the biomedical appliance or device is removed from the skin, little or no adhesive residue is left on the skin. Particularly preferred biomedical adhesives contemplated herein include the reaction product of dimer isocyanate or diisocyanate (DDI) and a nineteen carbon atom dihydroxy compound, hydroxymethyl octadecanol and the reaction product of DDI, bis hydroxyethyl dimerate (BHED) and a polyether tetrol designated "PeP 450".

DETAILED DESCRIPTION OF THE INVENTION

This invention is a biomedical appliance or device, as defined above, having a particularly advantageous skin compatible, advantageously aggressive adhesive disposed or placed on at least a portion of the operant surface thereof. The operant surface of a particular biomedical device for purposes of this invention is that part of the device intended to interact with or be in contact with (by means of the adhesive) a patient's skin. The particular choice of biomedical appliance or device on which to utilize the adhesive is well within the present level of skill in the relevant art. Thus, the remainder of this specification will be devoted to describing the biomedical adhesive. Ostomy appliances constitute a preferred utilization of the present adhesive.

In its essentials, the biomedical adhesive of the present invention consists essentially of the reaction product of a difunctional, fatty-acid-derived or fatty acid-based dimer and a suitable co-reactant. For purposes of illustration and not for purposes of limitation, the predominantly fatty acid dimer-derived component of the present adhesive composition can be represented by the general formula:

$$X—D—X \qquad (1)$$

wherein X represents, independently, a reactive functionality preferably selected from the group consisting of —OH, —COOH, COO⁻M⁻ where M⁻ is a metal cation such as Na⁻ or K⁻, amine, amide, ester, isocyanate, acid chloride, chloroformate, carbonate or mixtures thereof; and D is divalent, predominantly aliphatic, hydrocarbon radical of dimerized fat acid, D generally having from about 24 to 44 carbon atoms therein, and preferably having from about 32 to about 40 carbon atoms therein. These materials are more completely described in U.S. Pat. Nos. 3,493,534 to Coury et al, and, 3,549,570 to Coury, which are incorporated by reference herein.

The material which apparently provides many of the advantageous properties of the biomedical adhesive employed in the instant invention is the difunctional, fatty-acid-derived dimer. These materials are generally produced by the dimerization (e.g., by Diels-Alder-type reaction) of unsaturated, long chain fatty acid monomers. The monomers may be branched or linear and may be mono or polyunsaturated. Generally speaking, the monomeric fatty acids or fat acids have at least about 9 carbon atoms in their carbon backbones and may have upwards of 20 or more carbon atoms. Thus, where a true "dimer" is formed from two monomers, there will be approximately 18 to 40 or more carbon atoms in the resulting product.

A particularly well known source of fatty acid monomers from which the present difunctional dimers are based is tall oil. As described in "Tall Oil-Chemicals from a Natural, Renewable Source" by Benjamin F. Ward, Jr. in Applied Polymer Symposium. No. 28, 329 (1975), the pertinent portions of which are incorporated by reference herein, tall oil fatty acids are used to synthesize dimer acids (and dimer acid derivatives). These dimer acids have the unique advantages of being hydrophobic, high in molecular weight, generally having some degree of unsaturation and are dibasic. Both the unsaturation and the acid functionality provide sites from which further chemical modification may be undertaken. In practice, the degree of unsaturation of the dimer acid may be reduced by hydrogenation so as to enhance dimer stability.

A particularly preferred class of difunctional, fatty-acid derived dimers for use in the present invention is the dibasic dimer acids and derivatives or mixtures thereof. As described in The Dimer Acids, ed. Edward C. Leonard (1975 Humko Sheffied Chemical), the pertinent portions of which are incorporated by reference herein, dimer acids such as those produced by the dimerization of fatty acids having 18 or more carbon atoms are a mixture of 36-carbon atom dibasic acids, 54-carbon atom tribasic acid ("trimer acid"), 18 carbon atom monomer reactant and unpolymerized but structurally modified 18 carbon atom monobasic fatty acid. Thus it is to be understood that as the term "dimer" is used herein is intended to include all the potential reaction products of the fatty acid dimerization reaction whether exactly dimeric or even difunctional. Generally speaking, non-difunctional fractions should not exceed more than about 20 percent by weight of the "dimer" component. This definition of "dimer" is also intended to apply whether the material is a dimer acid or derivative thereof as more completely described below.

As described in Dimer Acids above, dimer acid (and therefore dimer acid derivative) is a complex mixture of geometic, structural (positional) and conformational isomers which is difficult to separate but which can be simplistically represented as follows:

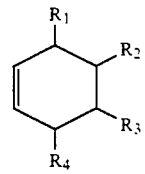

wherein $R_1$, $R_2$, $R_3$ or $R_4$ are separate and independent and either carboxyl-terminated or hydrocarbon-terminated depending upon the orientation of the fatty acid monomers during the dimerization reaction. Representative carboxy-terminated structures include: —(CH$_2$)$_8$COOH; —C≡CH(CH$_2$)$_8$COOH; —(CH$_2$)$_7$COOH; —CH$_2$CH═CH(CH$_2$)$_7$COOH; or —CH═CH(CH$_2$)$_7$COOH. Representative hydrocarbon-terminated structures include: CH$_3$(CH$_2$)$_4$—; CH$_3$(CH$_2$)$_5$—; CH$_3$(CH$_2$)$_7$—; CH$_3$(CH$_2$)$_4$CH═CH—; or CH$_3$(CH$_2$)$_4$CH═CHCH$_2$—.

It will be seen from the above that whether carboxy-terminated or hydrocarbon-terminated generally has at least about 4 carbon atoms in the $R_1$-$R_4$ groups. Bicyclic and tricyclic dibasic acid species produced by intramolecular dimerization of unsaturated reaction sites are also within the contemplated definition of dimer acid (and derivatives).

In addition to the dimer acid (or derivative) component of the present biomedical adhesive, the present invention also contemplates the utilization of dimer acid derivatives. For example, as described in Dimer Acids at pp. 56-80, dimer soaps (i.e., dimer acid salts), dimer esters, dimer amides, dimer glycols, dimer diisocyanates or essentially any other acid derivative which is sufficiently reactive are all within the contemplation of the present invention.

In order for the biomedical adhesive of the present invention to have the advantageous properties described herein, it is necessary for the dimer-based component to be reacted with a suitable second material referred to herein as a co-reactant or co-monomer. Generally speaking, the second reactant is one which reacts with the above described dimer fatty acid or derivative to produce a polymer also as described above. Without necessarily intending to be limited, it is believed the molecular weight of the resulting polymeric reaction product falls generally in the range of about 10,000 to 100,000. Preferably co-reactant functionalities include but are not limited to —OH, —COOH, —COO⁻M⁻, amine, amide or ester. The co-reactant can include a second fatty-acid dimer-based material as described above having different functionality. For example, a dimer diisocyanate could be reacted with a dimer diol to produce a polyurethane which would be essentially 100 percent fatty acid dimer-based.

Generally speaking, in order to obtain the advantageous properties, the resulting reaction/product polymer should be predominantly fatty acid dimer-derived. One of ordinary skill in the relevant art will recognize that the co-reactant selected will depend largely upon the dimer-based or dimer-derived material selected. Particularly preferred combinations of dimer-based materials and co-reactants are discussed in the examples.

The skin-compatible adhesive composition utilized in the present invention optionally contemplates the addition of a cross-linking agent such as glycerol or "Pluracol" PeP 450 polyether tetrol. Generally speaking, a cross-linking agent will be at least trifunctional and will tend to substantially increase the molecular weight and the internal cohesion of the resulting polymerized reaction product. It should be noted, however, that a cross-linking agent is not necessary to obtain the advantageous properties of the instant biomedical adhesive and would normally be employed in those situations where a high cohesive strength material is desired.

One of ordinary skill in the art will recognize that in order to obtain polymerization of the above-described co-reactants, catalysts or heat, separately or together, may be employed. For example, a particularly advantageous catalyst herein for the synthesis of polyurethanes is dibutyl tin dilaurate. Tetraalkyl titanates constitute another family of catalysts which may be utilized herein to synthesize polyesters. Alternatively, heat may be employed alone or in combination with the above described catalysts. Generally speaking, it is possible to heat the reactive monomers to a temperature in the range of 60° C. to 250° C. to obtain a fairly rapid polymerization to the resulting biomedical adhesive composition. The particular combination of catalysts or temperature to be employed in a the synthesis of a particular polymer is well known to one of ordinary skill in the relevant art.

The present invention also contemplates the utilization of additives to modify or enhance various desired properties of the polymeric reaction product. Additives which have been employed to enhance various properties (e.g., adhesion to wet surfaces and adhesive bond durability) include gelatin, pectin, sodium carboxymethyl cellulose, guar, karaya or dextran. Lastly, additives such as polyvinylpyrrolidone, the sodium salt of polyacrylic acid and sodium salt of 2-acrylamido-2-methyl propane sulfonic acid have been employed to enhance various properties.

Synthesis of the instant biomedical adhesive is relatively straightforward. Generally speaking, the respective co-reactants are intimately admixed at room temperature and heated under a nitrogen purge for a time period in the range of 1 to 5 hours. Shortly after heating is begun (or simultaneously therewith) a very small amount of appropriate catalyst is added to the mixture. The composition then is heated to a temperature in the range of 60° C. to 250° C. while continuing the nitrogen purge. Periodically, the head space above the reactant mixture may be evacuated and replaced with nitrogen.

The present invention will now be illustrated by a number of examples. The examples are intended to be illustrative of the present invention and not to be exhaustive. They should not be construed to limit the scope thereof. These examples will suggest, to one of ordinary skill in this art, many other ways in which the instant invention could be practiced, all of which are intended to be included within the scope of the claims which follow.

EXAMPLE I

Approximately 0.1 equivalent (14.57 grams) of hydroxymethyl octadecanol, available from Henkel Corporation (hereafter referred to as a C-19 diol) was mixed with 31.29 grams of dimer diisocyanate (0.1 equivalents) or dimer isocyanate (DDI 1410) commercially available from the Henkel Corporation. The two co-reactants were intimately mixed and two drops of dibutyl tin dilaurate polymerization catalyst were added. The mixture was heated for approximately two hours at a temperature of 70° C. The resulting polyurethane material was inherently tacky and did not readily flow at room temperature.

EXAMPLE II

Bis-hydroxyethyldimerate (BHED-commercially available from Emergy Industries) 18.6 grams was mixed with 0.8 grams of Pluracol "PeP450" polyether tetrol available from BASF Wyandotte Corporation. The "PeP450" is a tetra functional cross-linking agent. This mixture was then mixed with 20.0 grams of dimer diisocyanate (Henkel) along with two drops of dibutyl tin dilaurate polymerization catalyst. The resulting mixture was stirred, placed under vacuum, and left overnight under a nitrogen atmosphere. The resulting material was later found inherently tacky, self-supporting and formable at 175° F.

EXAMPLE III

One gram of 1,4 butane diol, 6.4 gram C-19 diol (hydroxymethyl octadecanol) and 10 grams of 360,000 molecular weight polyvinylpyrrolidone were stirred together. 20.0 grams dimer diisocyanate were added to the above mixture followed by two drops of dibutyl tin dilaurate polymerization catalyst. The resulting mixture was placed under vacuum at 139° F. and alternatively the vacuum was released and the mixture purged with nitrogen. Lastly, the vacuum was released and the mixture heated at 139° F. for three days under nitrogen purge. On the third day, the material was used to press out a pad or film which had a suitable modulus and tackiness.

EXAMPLE IV

Polytetramethylene ether glycol (32.8 grams) having an equivalent weight of approximately 496.5 ("Polymeg 1000" available from Quaker Oats) was mixed with 20 grams of dimer isocyanate along with two drops of dibutyl tin dilaurate. The mixture was placed in a vacuum oven at 139° F. and alternatively evacuated and purged with nitrogen while stirring. Continuing the nitrogen purge, the composition was heated over a weekend at the above temperature.

EXAMPLE V

A procedure of example IV was repeated with the substitution of 21.8 g "Teracol 650" (a 330.6 equivalent weight polyether) for "Polymeg 1000".

EXAMPLE VI

A polyurea composition of the present invention was prepared by mixing 20 grams of dimer amine (equivalent weight 275) commercially available from the Henkel Co. with 22 grams of dimer diisocyanate (equivalent weight 303.1) in the presence of approximately 20 gram of xylene solvent. The resulting material, upon removal of solvent, was high modulus and tacky.

EXAMPLE VII

A tacky polyamide composition of the present invention was prepared by mixing 20.0 grams of dimer acid (equivalent weight 285) with 21.27 grams of dimer isocyanate (equivalent weight 303.1) and heating the mixture at 120° C.

EXAMPLE VIII

Dimer isocyanate (30.01 g) (equivalent weight 300) and 5.905 grams of 1,6 hexanediol (equivalent weight 59.1) were heated in an oven to melt the hexanediol and obtain a liquid mixture. Two drops of polymerization catalyst (dibutyl tin dilaurate) were added with continued heating. The resulting material was fairly hard and had a relatively high modulus of elasticity. This material would likely be employed by blending with other adhesives or additives discussed above.

EXAMPLE IX

A material substantially the same as described in example III above was prepared with the exception that approximately 10 grams of the sodium salt of polyacrylic acid substituted for polyvinylpyrrolidone. The resulting mixture was heated to a temperature of 139° F. under nitrogen purge. The polymer was pressed at 175° F. into a low modulus tacky film.

EXAMPLE X

Materials substantially the same as that prepared in example III above was prepared with the exception that the 360,000 molecular weight polyvinylpyrrolidone was substituted with 10 grams of 40,000 molecular weight polyvinylpyrrolidone. The resulting material exhibited good tack.

EXAMPLE XI

A polyamide made of dimer isocyanate and dimer acid as described in example VII above was blended on a 50:50 weight percent basis with a polyurethane synthesized from dimer diisocyanate, bis-hydroxyethyl dimerate and PeP450. The blend was made by pressing the two materials together at a temperature of 350° F. The resulting material (which blended fairly uniformally) exhibited good tack and increased modulus over that of the polyamide alone.

EXAMPLE XII

Twenty grams of dimer diamine (equivalent weight 275) and 22 g of dimer isocyanate were mixed and reacted essentially instantaneously at room temperature without the addition of a catalyst.

EXAMPLE XIII

Dimer acid 130 g (equivalent weight 285) and 125 g dimer amine (equivalent weight 275) were reacted for a three hours at a temperature of 160° C. The reactants did not require the addition of a catalyst in order to produce the reaction product which had a relatively high modulus and was acceptably tacky.

EXAMPLE XIV

Karaya gum (2% by weight) was mixed with the reaction product of DDI, C-19 diol and PeP 450 to produce a material of the invention. The modulus of the material was low and exhibited high tack.

EXAMPLE XV

The material prepared in example I above was tested for its peel strength and coherence on skin and stainless steel. The material was pressed into place on a backing of "Volara" polyethylene foam and "Mylar" polyester film. The resulting backing with the biomedical adhesive thereon was then pressed into place on a stainless steel substrate for the purpose of measuring its 180° peel strength (ASTM Test Specification No. D-903-49 (reapproved 1978). On a 1/8 inch Volara foam backing utilizing an adhesive thickness of 0.001 in. the average of 5 peel strength measurements was 0.38 pounds per inch width (PPI) (standard deviation=0.093). At 1.5 mil adhesive thickness, peel strength was $0.94 \pm 0.184$ PPI. On a 1/32 in. "Volara" foam backing and 1 mil and 1 1/2 mil adhesive thickness, peel strengths of $1.27 \pm 0.107$ and $1.21 \pm 0.091$ PPI, respectively, were observed (5 measurements). On 0.004 in. "Mylar", a peel strengths of $2.01 \pm 0.033$ and $0.88 \pm 0.491$ PPI were observed for 1.0 and 1.5 mil adhesive.

The material as synthesized in example I above was employed to adhere circular electrocardiogram discs to the skin of several patients. These discs were held in place by the adhesive for time periods up to four days during which time the patients exercised and bathed normally.

These results indicate that the adhesive is a fairly hydrophobic, moisture-resistant material which did not substantially irritate skin during the time periods indicated. Further, when the discs were removed from the skin, no excoriation occurred. Excoriation commonly occurs with the pressure sensitive biomedical adhesives.

What is claimed is:

1. A biomedical apparatus comprising:
   (a) an operant surface adapted to be adhered to a patient's skin; and
   (b) a layer of adhesive on a portion of said operant surface, said adhesive a hydrophobic, polymeric, pressure sensitive, tacky, skin-compatible composition consisting essentially of the reaction product of:
     (1) a difunctional fatty acid-derived dimer of the structure X—D—X wherein X is a reactive functionality selected from the group consisting of amine, amide, ester, isocyanate, acid chloride, hydroxyl, carboxylic acid, chloroformate, and carbonate and D is a divalent, aliphatic nucleus resulting from the dimerization of long-chain fatty acids;
     (2) a compatible polymer-forming co-reactant, difunctional in groups reactive with said functionalities X and selected from the group consisting of amine, amide, ester, isocyanate, acid chloride, hydroxyl, carboxylic acid, chloroformate, and carbonate and said co-reactant having an aliphatic nucleus comprising about 18 carbon atoms or more;
     (3) between 0 and 10 equivalent percent of a crosslinking reactant which is at least trifunctional.

2. A biomedical apparatus as in claim 1 selected from ostomy appliances, electrodes, bandages, iontophoresis devices and transcutaneous electronic nerve stimulation devices.

3. An apparatus as in claim 1 wherein said difunctional co-reactant comprises at least 19 carbon atoms.

4. An apparatus as in claim 1 wherein said difunctional co-reactant is a difunctional dimer acid derivative.

5. An apparatus as in claim 1 wherein said reaction product consists of said fatty acid dimer component (a) and said co-reactant (b).

6. An apparatus as in claim 1 wherein said reaction product comprises a said crosslinking reactant (c) in an amount of between 2 and 4 equivalent percent.

7. An apparatus as in claim 1 wherein the reaction product has a molecular weight in the range of 10,000 to 100,000.

8. An apparatus as in claim 1 wherein the total of the fatty acid dimer and fatty acid dimer derivative content of the adhesive composition is between about 50 and about 99 weight percent.

9. An apparatus as in claim 1 wherein the adhesive composition further includes an additive selected from the group consisting of tackifiers, humectants, extenders, thixotropes and mixtures thereof.

10. An apparatus as in claim 1 wherein D contains from about 32 to 40 carbon atoms.

11. An apparatus as in claim 1 wherein the fatty acid-derived dimer is a diisocyanate and the co-reactant is a di-hydroxy compound.

12. An apparatus as in claim 1 wherein the co-reactant is bis-hydroxyethyldimerate.

13. An apparatus as in claim 1 wherein the co-reactant is hydroxymethyl octadecanol.

14. An apparatus as in claim 1 wherein the crosslinking reactant is glycerol.

15. An apparatus as in claim 1 wherein the crosslinking reactant is a polyether tetrol.

16. An apparatus according to claim 1 wherein the apparatus is an ostomy appliance.

17. An apparatus according to claim 1 wherein the apparatus is an electrode.

18. An apparatus according to claim 1 wherein the apparatus is surgical tape.

19. An apparatus according to claim 1 wherein the apparatus is a TENS device.

20. An apparatus according to claim 1 wherein the apparatus is an iontophoresis device.

21. A biomedical apparatus comprising:
  (a) an operant surface adapted to be adhered to a patient's skin; and
  (b) a layer of adhesive on a portion of said operant surface, said adhesive a hydrophobic, polymeric, pressure sensitive, tacky, skin-compatible composition consisting essentially of the reaction product of:
    (1) a difunctional fatty acid-derived dimer of the structure X—D—X wherein X is a reactive functionality selected from the group consisting of isocyanate, and hydroxyl and D is a divalent, aliphatic nucleus resulting from the dimerization of long-chain fatty acids;
    (2) a compatible polymer-forming co-reactant, difunctional in groups reactive with said functionalities X and selected from the group consisting of isocyanate and hydroxyl and said co-reactant having an aliphatic nucleus having at least about 18 carbon atoms;
    (3) between 0 and 10 equivalent percent of a crosslinking reactant which is at least trifunctional.

22. A biomedical apparatus according to claim 21 wherein the co-reactant compound is hydroxymethyl octadecanol.

23. A biomedical apparatus according to claim 21 wherein the co-reactant compound is bis-hydroxyethyl dimerate.

24. A biomedical apparatus according to claim 22 wherein the biomedical apparatus is an electrode.

25. A biomedical apparatus according to claim 21 wherein the biomedical apparatus is selected from the group consisting of ostomy appliances, electrodes, bandages, iontophoresis devices, and transcutaneous electronic nerve stimulation devices.

26. A biomedical apparatus according to claim 21 wherein said reaction product comprises between two percent and four percent of said crosslinking reactant.

27. A biomedical apparatus according to claim 21 wherein the reaction production has a molecular weight in the range of 10,000 to 100,000.

28. A biomedical apparatus according to claim 21 wherein the total of fatty acid dimer and fatty acid dimer derivative content of the adhesive composition is between about 50 and about 99 weight percent.

29. A biomedical apparatus according to claim 21 wherein the adhesive composition further includes an additive selected from the group consisting of tackifiers, humectants, extenders, thixotropes, and mixtures thereof.

30. A biomedical apparatus according to claim 21 wherein D contains from about 32 to 40 carbon atoms.

31. A biomedical apparatus according to claim 21 wherein the crosslinking reactant is glycerol.

32. A biomedical apparatus according to claim 21 wherein the crosslinking reactant is a polyether tetrol.

* * * * *